United States Patent [19]

Russell-Jones et al.

[11] Patent Number: 6,150,341
[45] Date of Patent: Nov. 21, 2000

[54] VITAMIN B$_{12}$ DERIVATIVES AND METHODS FOR THEIR PREPARATION

[75] Inventors: Gregory J. Russell-Jones; John F. McEwan, both of New South Wales, Australia

[73] Assignee: Biotch Australia Pty Limited, Roseville, Australia

[21] Appl. No.: 09/330,167

[22] Filed: Jun. 11, 1999

[30] Foreign Application Priority Data

Jun. 12, 1998 [AU] Australia ................................ PP 4050

[51] Int. Cl.$^7$ ..................................................... A61K 31/70
[52] U.S. Cl. .............................. 514/52; 514/12; 514/15; 424/193.1; 424/194.1; 422/61; 435/86
[58] Field of Search .................................. 514/2, 12, 15, 514/52; 424/193.1, 194.1; 422/61; 435/86

[56] References Cited

U.S. PATENT DOCUMENTS

| | | |
|---|---|---|
| 5,449,720 | 9/1995 | Russell-Jones et al. . |
| 5,548,064 | 8/1996 | Russell-Jones et al. ................. 530/380 |
| 5,574,018 | 11/1996 | Habberfield et al. ..................... 514/21 |
| 5,807,832 | 9/1998 | Russell-Jones et al. . |
| 5,863,900 | 1/1999 | Russell-Jones . |
| 5,869,466 | 2/1999 | Russell-Jones et al. . |
| 5,972,917 | 10/1999 | Bishop et al. . |

OTHER PUBLICATIONS

G.J. Russell–Jones et al., The Use of the Vitamin B$_{12}$ Transport System as a carrier for the Oral Delivery of Peptides, Proteins and Nanoparticles, Controlled Release Society, Inc., (1996), pp. 49, 50.

Anton et al., Carbon–13 Nuclear Magnetic Resonance Studies of the Monocarboxylic Acids of Cyanocobalamin. Assignments of the b–,d–, and e–Monocarbodylic Acids $^{1a}$, Journal of the American Chemical Society, (1980), pp. 2215–2219.

Russell–Jones et al., Vitamin B$^{12}$ Mediated Oral Delivery Systems for Granulocyte–Colony Stimulating Factor and Erythropoietin, Biconjungate Chem., vol. 6, No. 4 (1995), pp. 459–465.

Toraya et al., The Synthesis of Several Immobilized Derivatives of Vitamin B$_{12}$ Coenzyme and Their Use As Affinity Adsorbents for a Study of Interactions of Diol Dehydrase with the Coenzyme*, The Journal of Biological Chemistry, vol. 255, No. 8, (1980), pp. 3520–3525.

Annunziato et al., p–Maleimidophenyl Isocyanate: A Novem Heterobifunctional Linker for Hydroxyl to Thiol Coupling, Biioconjugate Chem, (1993), pp. 212–218.

*Primary Examiner*—James O. Wilson
*Attorney, Agent, or Firm*—Foley & Lardner

[57] ABSTRACT

This invention relates to methods for preparing vitamin B$_{12}$ (VB$_{12}$) derivatives suitable for linking to a polymer, nanoparticle or therapeutic agent, protein or peptide. The methods involve reacting the 5'OH group of VB$_{12}$ or an analogue thereof with an active carbonyl electrophile and subsequently obtaining said VB$_{12}$ derivatives. The invention also relates to novel VB$_{12}$ derivatives, VB$_{12}$ derivatives prepared by the methods of the present invention and uses thereof in the preparation of in the preparation of polymer complexes or nanoparticles.

26 Claims, 1 Drawing Sheet

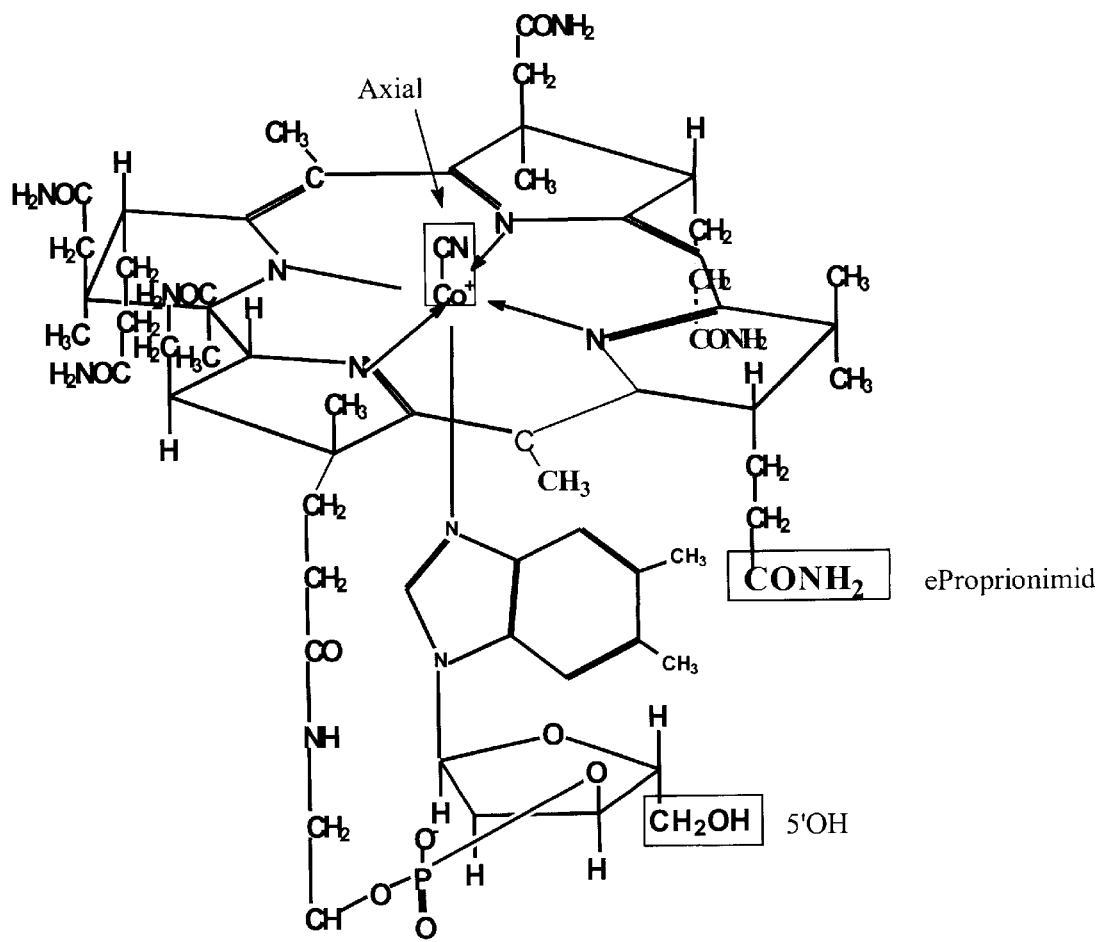
Figure 1. Conjugation sites of $VB_{12}$ ized monocarboxylic acid derivatives can
VITAMIN B₁₂ DERIVATIVES AND METHODS FOR THEIR PREPARATION

TECHNICAL FIELD

The present invention generally relates to novel derivatives of vitamin $B_{12}$ carrier molecules for the delivery of therapeutic substances by administration of a complex comprising these substances linked to vitamin $B_{12}$ ($VB_{12}$) or an analogue thereof. The invention also generally relates to novel methods for preparing $VB_{12}$ derivatives. More particularly, the invention relates to reactions of the 5'OH group of $VB_{12}$ with electrophiles to prepare these $VB_{12}$ derivatives.

BACKGROUND OF THE INVENTION

An oral delivery mechanism for peptides is described in International application PCT/AU86/0299 (WO87/02251) based on recent work undertaken by one of the current inventors. The mechanism utilises at least one carrier molecule to which an active substance is linked to transport the active substance from the intestinal lumen into the circulatory system. $VB_{12}$ and analogues thereof function as ideal carrier molecules by using the natural $VB_{12}$ uptake system, mediated by the binding of $VB_{12}$ to intrinsic factor (IF), to transport the active substance/$VB_{12}$ complex. Once delivered into the lymphatic drainage system or serum, the complex substantially retains the bioactivity of the native active substance.

More recently conjugates of $VB_{12}$ with drugs, cytotoxins and MRI agents, have been used in the detection and treatment of tumour cells. For normal cellular uptake of vitamin $B_{12}$ (cobalamin, Cbl, $VB_{12}$), the vitamin must first bind to the plasma protein transcolbamin II (TCII). Following binding of Cbl to TCII the resultant TCII-Cbl complex binds with high affinity to receptors on the surface of cells and is internalized by the cell via a process called receptor-mediated endocytosis (RME). Once inside the cell the Cbl is enzymatically modified to form two coenzymes, which are in turn used for two essential metabolic pathways. One pathway involves the methylation of homocysteine in the de novo synthesis of methionine, and is catalyzed by methionine synthase. The other pathway involves the rearrangement of methylmalonyl CoA to succinyl CoA, and is catalyzed by methylmalonyl CoA mutase. It has recently been shown that the in vitro proliferation of human and murine leukemia cells is dependent upon both TCII and Cbl (McLean, G. R., Quadros, E. B., Rothenberg, S. P., Morgan, A. C., Schrader, J. W., and Ziltener, H. J., 1997 Antibodies to transcobalamin II block in vitro proliferation of leukemic cells, *Blood*, 89, 235–242). Several workers have now concentrated on utilizing Cbl conjugates for both radio-imaging and for targeted cancer chemotherapy (Smeltzer, C. C., Pinson, P. R., Munger, J. M., West, F. G., and Grissom, C. B., 1999 Cytotoxicities of two new cobalamin bioconjugates. *Proceedings Ninth International Symposium on Recent Advances in Drug Delivery Systems*, pp 232–3; Canon, M. J., Munger, J. M., West, F. G., and Grissom, C. B., 1999 Synthesis and uptake of radiolabeled cobalamin bioconjugate, *Proceedings Ninth International Symposium on Recent Advances in Drug Delivery Systems*, pp 230–1; Pinson, P. R., Munger, J. M., West, F. G., and Grissom, C. B., 1999 Synthesis of two doxorubicin-cobalamin bioconjugates, *Proceedings Ninth International Symposium on Recent Advances in Drug Delivery Systems*, pp 228–9).

In order for $VB_{12}$ to co-transport pharmaceuticals across the intestinal epithelial cell layer and into the circulatory system the pharmaceuticals must first be covalently linked to the $VB_{12}$ molecule. Similarly, in order that $VB_{12}$ can target an anti-tumour agent to a tumour, the agent must also be covalently linked to the $VB_{12}$ molecule. For this to occur, the $VB_{12}$ molecule itself must first be modified to provide a suitable functional group for conjugation. A carboxylic acid derivative of $VB_{12}$ is readily achieved by mild acid hydrolysis of the propionimide side chains of the corrin ring structure[1] (see FIG. 1). This hydrolysis results in the formation of the "b", "d" and "e" monocarboxylic acids of $VB_{12}$.[2] The isolated monocarboxylic acid derivatives can then be conjugated directly to amino groups of proteins or peptides using commercial carbodiimides such as 1-ethyl-3-(3-(dimethylamino)propyl)carbodiimide (EDAC) or dicyclohexylcarbodiimide (DCC) thereby linking the peptide to $VB_{12}$ via a peptide bond.[1,3]

A second method of conjugation of peptides to $VB_{12}$ is by axial substitution of functional groups onto the Co atom of the corrin ring of the $VB_{12}$ molecule (see Formula 1). In this method, the axial CN ligand of $VB_{12}$ can be replaced with a functionalised alkyl chain. This substituted functional group can then be used for conjugation to a peptide or protein using traditional chemical techniques. One major disadvantage of this method, however, is that the resultant conjugate contains a light sensitive Co—C bond. Thus care must be taken not to expose solutions of the alkylcobalamins to visible light.

Early work by Toraya and Fukui[4] demonstrated the feasibility of conjugation to $VB_{12}$ via an ester linkage to the 5'OH of the ribose moiety of the nucleotide ligand. In their work Toraya and Fukui explored the possibility of using this chemistry to form an affinity ligand for purification of diol dehydrase. In order to form the 5'O-ester linkage the authors reacted $VB_{12}$ with a 54 fold excess of succinic anhydride in a large volume of DMSO ($VB_{12}$ at 5 mg/ml) plus a large excess of pyridine (128 fold w/w). These authors found that the linkage formed was not only unstable at basic pH, but was also ineffective in purifying the enzyme. Annunziato and co-workers[5] describe another method of linkage to the 5'OH of the ribose. These workers reacted p-maleimidophenyl isocyanate with $VB_{12}$ and subsequently used the activated $VB_{12}$ molecule to react with thiolated alkaline phosphatase. Subsequently, Habberfield and co-workers combined the work of Toraya and Fukui[4] with that of Annunziato et al.,[5] as well as Russell-Jones et al.[3,6] and produced conjugates of G-CSF, EPO and consensus interferon to a 5'O-glutaroyl derivative of $VB_{12}$. The subsequent conjugates were claimed to be active following intraduodenal pump administration to rats of the conjugates pre-complexed to rat IF. In the method described by Habberfield and co-workers, 5 gm of cyanocobalamin ($VB_{12}$– 1356 MW) was dissolved in 1,000 ml of DMSO and 200 gm of glutaric anhydride (116 MW) was added in 160 ml of pyridine. The product yield was around 65%. This represents a 468 molar excess of glutaric anhydride to $VB_{12}$. In the work of Toraya and Fukui,[4] these workers used 200 mg of cyanocobalamin dissolved in 40 ml DMSO plus 8 grams of succinic anhydride (100 MW) to couple to the hydroxyl group. This represents a 54 fold molar excess of anhydride, with a product yield of 90%. In the method of conjugation described by Russell-Jones and co-workers[3,6] the $VB_{12}$ monoacid was prepared by treatment with acid for 72 hrs and subsequent purification on Dowex 1×8 and Dowex 1×2 to afford a yield of only about 5%. In order to link the $VB_{12}$ monoacid to some peptides and proteins further derivatization of the carboxyl group was often required.

Apart from the methods described by Toraya and Fukui[4] and Habberfield et al[7] and Annunziato et al.,[5] there are other methods which could be used to form covalent linkages to the 5'OH group of $VB_{12}$. These methods are generally used in the preparation of affinity resins by modification of sugar residues resident in agarose. These methods include reaction with oxirane (1,4 butane-diol diglycidyl ether), benzoquinone or cyanuric chloride. These methods have been attempted in the synthesis of $VB_{12}$ derivatives, however, the yields were either so low as to make the process non-commercial, or the quantities of reagents employed were so high as to make them similarly non-commercial.

Thus it is an object of the present invention to overcome, or at least alleviate one or more of the abovementioned disadvantages of the prior art. In particular, it is an object of the present invention to provide novel methods for preparing derivatives of $VB_{12}$ carrier molecules which utilise the 5'OH group of $VB_{12}$ for chemical bonding with spacer molecules. It is a preferred object of the present invention that the $VB_{12}$ derivatives are easy to make, obtained in good to high yields and readily purified.

SUMMARY OF THE INVENTION

Surprisingly it has been found by the present inventors that $VB_{12}$ derivatives, which are suitable for conjugation to polymers, nanoparticles and pharmaceutically active agents, are readily prepared by reaction of the 5'OH group on the ribose moiety of $VB_{12}$ with carbonyl electrophiles.

According to an aspect of the present invention there is provided a method for preparing $VB_{12}$ derivatives suitable for linking to a polymer, nanoparticle or therapeutic agent, protein or peptide comprising the steps of reacting the 5'OH group of $VB_{12}$ or an analogue thereof with a bifunctional carbonyl electrophile to form an active intermediate, and subsequently reacting the intermediate with a nucleophilic spacer molecule to yield said $VB_{12}$ derivative.

According to another aspect of the present invention there is provided a method for preparing a $VB_{12}$ derivative suitable for linking to a polymer, nanoparticle or therapeutic agent, protein or peptide comprising the steps of reacting a carboxylic acid spacer molecule with a bifunctional carbonyl electrophile to form an active intermediate, and subsequently reacting the 5'OH group of $VB_{12}$ with the active intermediate to yield said $VB_{12}$ derivative.

There are also provided derivatives of $VB_{12}$ prepared by the methods of the present invention. These derivatives are ideally linked to a biocompatible polymer or associated with a nanoparticle. These polymers and nanoparticles may be mixed with pharmaceutically acceptable carriers and/or diluents to provide pharmaceutical compositions for therapeutic administration to subjects.

Throughout this specification and the claims which follow, unless the text requires otherwise, the word "comprise", and variations such as "comprises" or "comprising", will be understood to imply the inclusion of a stated integer or step or group of integers or steps but not the exclusion of any other integer or step or group of integers or steps.

BRIEF DESCRIPTION OF THE FIGURE

The present invention will now be described with reference to the FIGURE wherein:

FIG. 1 is a representation of a $VB_{12}$ molecule showing three sites for the possible conjugation of agents and peptides to $VB_{12}$. These sites of conjugation are as follows:

a) axial conjugation through substitution onto the Co atom of the corrin ring;

b) direct conjugation following acid modification of the ePropianimide side chain; and c) conjugation to the 5'OH group of the ribose moiety of the nucleotide residue.

DETAILED DESCRIPTION OF THE INVENTION

The $VB_{12}$ derivatives of the present invention are suitable for conjugation or linking to polymers, nanoparticles, therapeutic agents, proteins and peptides and other such pharmaceutically active agents. The methods for the production of these $VB_{12}$ derivatives enable the derivatives to be obtained in generally good to high yields and are of good purity.

In general these derivatives are obtained by dissolving $VB_{12}$ or an analogue thereof in a solvent, preferably a suitable non-aqueous solvent such as dry DMF, dry THF or dry DMSO, and activating the 5'OH group of $VB_{12}$ by reaction with a carbonyl electrophile, preferably 1,1'-carbonyldiimidazole at 1–5 molar excess. Quantities above 5 molar excess may be used, however this is generally not required. Preferably $VB_{12}$ is dissolved at high concentration in DMSO. The activated $VB_{12}$ intermediate may then be coupled directly to peptides or proteins, or may be reacted with diamino-spacers, or amino-spacer-acids, or alternatively with amino-alkyl chains to form hydrophobic derivatives of $VB_{12}$ suitable for insertion into the hydrophobic surface of micro- or nanoparticles or into lipids or liposomes.

An alternative method of this invention also utilises the 5'OH group of $VB_{12}$ in the production of 5'OH ester derivatives of $VB_{12}$. In the synthesis of the 5'OH ester derivatives an active electrophilic intermediate is first prepared from the reaction of a carboxylic acid spacer molecule with a bifunctional carbonyl electrophile to prepare the active electrophilic intermediate. $VB_{12}$ or analogues thereof are then subjected to reaction with the electrophilic intermediate whereby the 5'OH group of $VB_{12}$ attacks the carbonyl electrophile and displaces a leaving group to yield the $VB_{12}$ derivative. The $VB_{12}$ is preferably linked to an amino acid spacer or to an acid lipid in the preparation of the 5'OH ester derivative of $VB_{12}$. These derivatives have the added advantage that they are easy to make and produce spacers, or linkages that are readily cleaved by serum esterases to regenerate the native $VB_{12}$ in vivo.

The present inventors have utilised carbonyl electrophiles to enable attack of the weak 5'OH nucleophile by the strongly electropositive carbonyl group in combination with good leaving groups attached to the carbonyl group. The methods overcome problems in the prior art where strong basis have been used to attach cross-linking agents to the $VB_{12}$ molecule, these strong base of which can denature the $VB_{12}$.

In a preferred embodiment, the carbonyl electrophile is a bifunctional carbonyl electrophile selected from carbonyldiimidazole, phosgene, triphosgene, N,N'-disuccinimidyl carbonate, carbonyl dipiperidine, 1,1'-carbonyldi(1,2,4-triazole), di(2-pyridyl)ketone, or di(1-benzotriazolyl)carbonate, more preferably carbonyldiimidazole.

The present invention also provides a $VB_{12}$ derivatives of the formula (I):

$$VB_{12}\text{-}5'O\text{—}CO\text{—}NH\text{—}R^1 \qquad (I)$$

or a salt thereof, wherein $R^1$ is $C_{1-24}$alkyl, $C_{2-24}$alkenyl, $C_{2-24}$alkynyl, $C_{3-8}$cycloalkyl, $(C_{3-8}$cycloalkyl)alkyl, amino, —(C

$_{12}$alkyl)C(O)R$^2$, —(C$_{2-12}$alkenyl)C(O)R$^2$, —NHC(O)—C$_{1-8}$alkyl-C(O)NHNH$_2$ or —CH(R$^3$)C(O)R$^4$ all of which optionally may be substituted by one or more groups selected from amino, amido, hydroxy, alkyl, halo, haloalkyl, carboxy, alkoxycarbonyl, acetoxy, sulfanyl, aryl, arylalkyl and alkylarylalkyl, R$^2$ is amino, hydroxy, C$_{1-6}$alkoxy or C$_{2-6}$alkenyloxy, R$^3$ is an amino acid side chain or a derivative thereof, and R$^4$ is hydroxy, C$_{1-6}$alkoxy, an amino acid or a peptide.

Preferably R$^1$ is hexyl, dodecyl, tetradecyl, hexadecyl, octadecyl, aminoethyl, aminobutyl, aminohexyl, aminododecanyl, t-butyl-Phe, succinylhydrazidyl, adipylhydrazidyl, Gly-OMe or Gly-OH.

The present invention also provides a VB$_{12}$ derivative of the formula (II):

$$VB_{12}\text{-5'O—CO—R}^1 \qquad (II)$$

or a salt thereof, wherein

R$^1$ is C$_{1-24}$alkyl or C$_{2-24}$alkenyl optionally which may be substituted by one or more groups selected from amino, amido, hydroxy, alkyl, halo, haloalkyl, carboxy, alkoxycarbonyl, acetoxy, sulfanyl, aryl, arylalkyl and alkylarylalkyl, or R$^1$ is —CH(R$^2$)—NHR$^3$, R$^2$ is an amino acid side chain or derivative thereof, and R$^3$ is hydrogen, an amine protecting group, an amino acid or a peptide.

Preferably R$^1$ is C$_{8-24}$alkyl, C$_{8-24}$alkenyl, or —CH(R$^2$)—NHR$^3$ where R$^2$ is glycine and R$^3$ is Boc or hydrogen, or R$^2$ is phenylalanine and R$^3$ is Boc or hydrogen. It will be apparent to one skilled in the art that other amino acids or proteins can be used to derivatise the VB$_{12}$ molecule or analogues thereof. Furthermore, it will be apparent that the amino acids or proteins may require protection of pendant functional groups or other such masking prior to subjecting these reactants to the coupling reactions of the present invention.

The VB$_{12}$ derivatives of the present invention may be linked to polymers or associated with nanoparticles or the like to prepare vitamin complexes according to standard methods known to those skilled in the art and published in the patent and scientific literature. Examples of such methods may be found in, for example, European Patent No. 0 220 030, Australian Patent No. 664365 and U.S. Pat. Nos. 5,449,720 and 5,548,064.

The vitamin complexes are used to deliver agents or active substances, in particular hormones, drugs, prodrugs, enzymes, proteins, peptides, toxins, immunogens or DNA or RNA analogues to subjects. Subjects are preferably vertebrate hosts, more preferably veterinary, domestic and agricultural animals and humans.

The polymers or nanoparticles prepared from the VB$_{12}$ derivatives of the present invention may be formulated as a pharmnaceutical composition by combining the polymers or nanoparticles with a pharmaceutically acceptable carrier and/or diluent in accordance with standard formulation techniques known to those skilled in the art. The pharmaceutical compositions may be formulated in any acceptable way to meet the desired mode of administration as determined by those skilled in the art.

Major advantages of the methods taught in this specification include the increase in yield of the VB$_{12}$ derivatives, and cost savings due to the reduction in chemicals used during the activation of the VB$_{12}$ or the incoming activated acid.

The present invention is further described with reference to the following examples which are in no way limiting on the scope of the invention.

EXAMPLE 1

Preparation of 5'OH-(hexyl)-VB$_{12}$

Materials: VB$_{12}$ was obtained from Rousell-Uclaf.

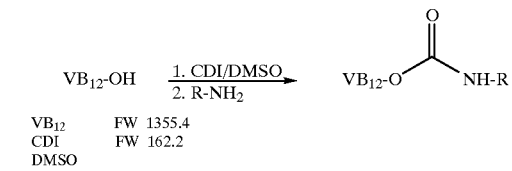

| VB$_{12}$ | FW 1355.4 |
| CDI | FW 162.2 |
| DMSO | |

Solid 1,1'-carbonyldiimidazole (CDI, 260 mg) was added to cyanocobalamin (1.0 g, 0.74 mmol) previously dissolved in dimethylsulfoxide (12 mL) at 30° C. and the mixture stirred for 25 min. Hexylamine (2.7 mmol) was added in one portion and stirring continued for a further 24 h at room temperature. The mixture was extracted with phenol/dichloromethane (1:1, 2×20 mL) and back extracted with water (2×20 mL from 1:4 phenol/dichloromethane). The mixture was purified by phenyl sepharose (50 g) column chromatography, eluting the unmodified VB$_{12}$ with 25% ethanol and the product with 60% ethanol. The solvent was removed at reduced pressure and the residue was resuspended by sonication for 5 min into acetone (50 mL). The mixture was filtered and the solid washed with acetone and air dried: yield, 60%; mp 213–215° C. (dec); MS (ESI) mass calcd for C$_{70}$H$_{101}$N$_{15}$O$_{15}$CoP 1482, found 1505 (M+23)$^+$; UV (H$_2$O)$\lambda_{361}$ ($\epsilon$=10500).

EXAMPLE 2

Preparation of 5'OH-(dodecyl)-VB$_{12}$

Solid 1,1'-carbonyldiimidazole (CDI, 260 mg) was added to cyanocobalamin (1.0 g, 0.74 mmol) previously dissolved in dimethylsulfoxide (12 mL) at 30° C. and the mixture stirred for 25 min. Dodecylamine (2.7 mmol) was added in one portion and stirring continued for a further 24 h at room temperature. The mixture was extracted with phenol/dichloromethane (1:1, 2×20 mL) and back extracted with water (2×20 mL from 1:4 phenol/dichloromethane). The mixture was purified by phenyl sepharose (50 g) column chromatography, eluting the unmodified VB$_{12}$ with 25% ethanol and the product with 60% ethanol. The solvent was removed at reduced pressure and the residue was resuspended by sonicated for 5 min into acetone (50 mL). The mixture was filtered and the solid washed with acetone and air dried: yield, 52%; mp 215–218° C. (dec); MS (ESI) mass calcd for C$_{76}$H$_{113}$N$_{15}$O$_{15}$CoP 1566, found 1589 (M+23)$^+$; UV (H$_2$O)$\lambda_{361}$ ($\epsilon$=16900).

EXAMPLE 3

Preparation of 5'OH-(tetradecyl)-VB$_{12}$

Solid 1,1'-carbonyldiimidazole (CDI, 260 mg) was added to cyanocobalamin (1.0 g, 0.74 mmol) previously dissolved in dimethylsulfoxide (12 mL) at 30° C. and the mixture stirred for 25 min. Tetradecylamine (2.7 mmol) was added in one portion and stirring continued for a further 24 h at room temperature. The mixture was extracted with phenol/dichloromethane (1:1, 2×20 mL) and back extracted with water (2×20 mL from 1:4 phenol/dichloromethane). The mixture was purified by phenyl sepharose (50 g) column chromatography, eluting the unmodified VB$_{12}$ with 25% ethanol and the product with 60% ethanol. The solvent was removed at reduced pressure and the residue resuspended by sonication for 5 min into acetone (50 mL). The mixture was filtered and the solid washed with acetone and air dried: yield, 46%; mp 228–233° C. (dec); MS (ESI) mass calcd for $C_{78}H_{119}N_{15}O_{15}CoP$ 1595, found 1618 $(M+23)^+$; UV ($H_2O$) $\lambda_{361}$ ($\epsilon=13000$).

EXAMPLE 4
Preparation of 5'OH-(hexadecyl)-$VB_{12}$

Solid 1,1'-carbonyldiimidazole (CDI, 260 mg) was added to cyanocobalamin (1.0 g, 0.74 mmol) previously dissolved in dimethylsulfoxide (12 mL) at 30° C. and the mixture stirred for 25 min. Hexadecylamine (2.7 mmol) was added in one portion and stirring continued for a further 24 h at room temperature. The mixture was extracted with phenol/dichloromethane (1:1, 2×20 mL) and back extracted with water (2×20 mL from 1:4 phenol/dichloromethane). The mixture was purified by phenyl sepharose (50 g) column chromatography, eluting the unmodified $VB_{12}$ with 25% ethanol and the product with 60% ethanol. The solvent was removed at reduced pressure and the residue was sonicated for 5 min into acetone (50 mL). The mixture was filtered and the solid washed with acetone and air dried: yield, 48%; mp 223–227° C. (dec); MS (ESI) mass calcd for $C_{80}H_{121}N_{15}O_{15}CoP$ 1623, found 1646 $(M+23)^+$; UV ($H_2O$) $\lambda_{361}$ ($\epsilon=20000$).

EXAMPLE 5
Preparation of 5'OH-(octadecyl)-$VB_{12}$

Materials: $VB_{12}$ was obtained from Rousell-Uclaf.

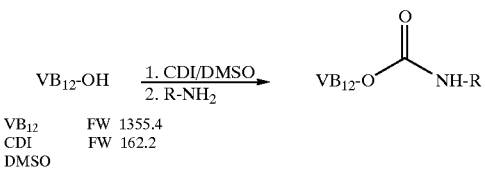

| | FW |
|---|---|
| $VB_{12}$ | 1355.4 |
| CDI | 162.2 |
| DMSO | |

$VB_{12}$ (1.0 g, 1.0 equivalent) was dissolved in dry DMSO (20 ml) at room temperature. Solid carbonyldiimidazole (CDI; 400 mg, 3.3 equivalents) was added and the mixture stirred at room temperature for 1 hr. The reaction mix was split into 4 equal parts and added to 500 mg of octadecylamine (Aldrich) dissolved in acetone, ethanol, dichloromethane or chloroform. The reaction was allowed to proceed for 2 hours after which the reaction was monitored by TLC and RP-HPLC to determine the quantity of product (5'OH-(octadecyl)-$VB_{12}$) which was formed.

The product was then separated from the unreacted $VB_{12}$ by addition of an equal volume of water and DCM, followed by centrifugation in a Beckman high speed (5K, 10 min). The DCM phase was removed and the product separated from unmodified $VB_{12}$ by flash column chromatography (isopropanol 50%, ammonia 2%, water 48%) then lyophilysed: yield, 66%; mp 220–223° C. (dec); MS (ESI) mass calcd for $C_{82}H_{125}N_{15}O_{15}CoP$ 1651, found 1674 $(M+23)^+$; UV ($H_2O$)$\lambda_{361}$ ($\epsilon=17500$).

EXAMPLE 6
Preparation of 5'OH-(aminoethyl)-$VB_{12}$ $VB_{12}$ (1.0 g, 1.0 equivalent) was dissolved in dry DMSO (20 ml) at room temperature. Solid carbonyldiimidazole (CDI; 400 mg, 3.3 equivalents) was added and the mixture stirred at room temperature for 1 hr. Diaminoethane (3.3 equiv) was added to the reaction mix. The mixture was stirred for 12 h and then poured into acetone/ethyl acetate (1:1, 200 mL) and left to stand. The supernatant was poured off and the residue resuspended in acetone (50 mL) by sonicationed for 5 min. The mixture was filtered onto a sintered glass funnel and the solid washed with acetone. The product was purified by Flash chromatography on a silica column using isopropanol 50%, ammonia 2%, water 48%. The product was then lyophilysed: yield, 63%; mp 206–210° C. (dec); TLC (${}^i$PrOH 30/n-BuOH 45/$H_2O$ 25/$NH_4OH$ 2) $R_f$=0.22; MS (ESI) mass calcd for $C_{66}H_{94}N_{16O15}CoP$ 1441, found 1441 $(M)^+$; UV ($H_2O$)$\lambda_{361}$ ($\epsilon=19900$).

EXAMPLE 7
Preparation of 5'OH-(aminobutyl)-$VB_{12}$ $VB_{12}$ (1.0 g, 1.0 equivalent) was dissolved in DMSO (35 mL) at room temperature. Solid carbonylduimidazole (CDI; 400 mg, 3.3 equivalents) was added and the mixture stirred at room temperature for 1 hr. Solid diaminobutane (3.3 equiv) was added in one portion. The mixture was stirred for 12 h and then poured into acetone/ethyl acetate (1:1, 200 mL) and left to stand. The supernatant was poured off and the residue in acetone (50 mL) sonicated for 5 min. The mixture was filtered onto a sintered glass funnel and the solid washed with acetone. The product was purified by column chromatography (silica, isopropanol 50%, ammonia 2%, water 48%) then lyophilysed: yield, 70%; mp 242–244° C. (dec); TLC (${}^i$PrOH 30/n-BuOH 45/$H_2O$ 25/$NH_4OH$ 2) $R_f$=0.08; MS (ESI) mass calcd for $C_{68}H_{98}N_{16}O_{15}CoP$ 1469, found 1469 $(M)^+$; UV ($H_2O$)$\lambda_{361}$ ($\epsilon=15500$).

EXAMPLE 8
Preparation of 5'OH-(t-butyl-Phe)-$VB_{12}$ $VB_{12}$ (1.0 g, 1.0 equivalent) was dissolved in DMSO (35 mL) at room temperature. Solid carbonyldiimidazole (CDI; 400 mg, 3.3 equivalents) was added and the mixture stirred at room temperature for 1 hr. Solid t-butyl-Phe (3.3 equiv) was added in one portion. The mixture was stirred for 12 h and then poured into acetone/ethyl acetate (1:1, 200 mL) and left to stand. The supernatant was poured off and the residue in acetone (50 mL) sonicated for 5 min. The mixture was filtered onto a sintered glass funnel and the solid washed with acetone. The product was purified by Flash column chromatography (silica, isopropanol 50%, ammonia 2%, water 48%) then lyophilysed.

EXAMPLE 9
Preparation of 5'OH-(aminohexyl)-$VB_{12}$ $VB_{12}$ (1.0 g, 1.0 equivalent) was dissolved in dry DMSO (20 ml) at room temperature. Solid carbonyldiimidazole (CDI; 400 mg, 3.3 equivalents) was added and the mixture stirred at room temperature for 1 hr. Diaminohexane (3.3 equiv) was added to the reaction mix as a solid. The mixture was stirred for 12 h and then poured into acetone/ethyl acetate (1:1, 200 mL) and left to stand. The supernatant was poured off and the residue in acetone (50 mL) sonicated for 5 min. The mixture was filtered onto a sintered glass funnel and the solid washed with acetone. The product was purified by column chromatography (isopropanol 50%, ammonia 2%, water 48%) then lyophilysed: yield, 98%; mp 230–233° C. (dec); TLC (${}^i$PrOH 30/n-BuOH 45/$H_2O$ 25/$NH_4OH$ 2) $R_f$=0.11; MS (ESI) mass calcd for $C_{70}H_{102}N_{16}O_{15}CoP$ 1497, found 1497 $(M)^+$; UV ($H_2O$)$\lambda_{361}$ ($\epsilon=17000$).

EXAMPLE 10
Preparation of 5'OH-(aminododecanyl)-$VB_{12}$ $VB_{12}$ (1.0 g, 1.0 equivalent) was dissolved in DMSO (35 mL) at room temperature. Solid carbonyldiimidazole (CDI; 400 mg, 3.3 equivalents) was added and the mixture stirred at room temperature for 1 byhr. followed by addition of diaminododecane (3.3 equiv) in one portion. The mixture was stirred for 12 h and then poured into acetone/ethyl acetate (1:1, 200 mL) and left to stand. The supernatant was poured off and the residue resuspended in acetone (50 mL) and sonicated for 5 min. The mixture was filtered onto a sintered glass funnel and the solid washed with acetone. The product was purified by Flash column chromatography (silica resin using isopropanol 50%, ammonia 2%, water 48%) then lyophilysed: yield, 68%; mp 156–158° C. (dec); TLC ($^i$PrOH 30/n-BuOH 45/$H_2$O 25/$NH_4$OH 2) $R_f$=0.27; MS (ESI) mass calcd for $C_{76}H_{114}N_{16}O_{15}CoP$ 1581, found 1581 (M)$^+$; UV ($H_2O$)$\lambda_{361}$ ($\epsilon$=33000).

EXAMPLE 11
Preparation of 5'OH-(succinylhydrazidyl)-$VB_{12}$ $VB_{12}$ (1.0 g, 1.0 equivalent) was dissolved in DMSO (35 mL) at room temperature. Solid carbonyldiimidazole (CDI; 400 mg, 3.3 equivalents) was added and the mixture stirred at room temperature for 1 hr followed by solid succinyldihydrazide (3.3 equiv) added in one portion. The mixture was stirred for 12 h and then poured into acetone/ethyl acetate (1:1, 200 mL) and left to stand. The supernatant was poured off and the residue in acetone (50 mL) sonicated for 5 min. The mixture was filtered onto a sintered glass funnel and the solid washed with acetone. The product was purified by Flash column chromatography (isopropanol 50%, ammonia 2%, water 48%) then lyophilysed: yield, 68%; mp 206–208° C. (dec); TLC ($^i$PrOH 30/n-BuOH 45/$H_2$O 25/$NH_4$OH 2) $R_f$=0.36; MS (ESI) mass calcd for $C_{68}H_{96}N_{18}O_{17}CoP$ 1581, found 1581 (M)$^+$; UV ($H_2O$)$\lambda_{361}$ ($\epsilon$=15700).

EXAMPLE 12
Preparation of 5'OH-(adipylhydrazidyl)-$VB_{12}$ $VB_{12}$ (1.0 g, 1.0 equivalent) was dissolved in DMSO (35 mL) at room temperature. Solid carbonyldiimidazole (CDI; 400 mg, 3.3 equivalents) was added and the mixture stirred at room temperature for 1 hr followed by solid adipyldihydrazide (3.3 equiv) added in one portion. The mixture was stirred for 12 h and then poured into acetone/ethyl acetate (1:1, 200 mL) and left to stand. The supernatant was poured off and the residue in acetone (50 mL) sonicated for 5 min. The mixture was filtered onto a sintered glass funnel and the solid washed with acetone. The product was purified by silica column Flash chromatography (isopropanol 50%, ammonia 2%, water 48%) then lyophilyzed: yield, 73%; mp 208–210° C. (dec); TLC ($^i$PrOH 30/n-BuOH 45/$H_2$O 25/$NH_4$OH 2) $R_f$=0.33; MS (ESI) mass calcd for $C_{70}H_{100}N_{18}O_{17}CoP$ 1555, found 1555 (M)$^+$; UV ($H_2O$)$\lambda_{361}$ ($\epsilon$=21100).

EXAMPLE 13
Preparation of ester-linked $VB_{12}$-phenylalanine

Boc-phenylalanine (1.57 g, 0.0059 mol) and carbonyl diimidazole (1.01 g, 0.0062 mol) were dissolved in DMF (6 ml) and the solution stirred at room temperature for 1 h with vigorous evolution of $CO_2$. A solution of $VB_{12}$ (1.0 g) in DMSO (10 ml) was added dropwise to the active ester solution followed by DIEA (1.2 ml, 0.89 g, 0.0069 mol) and stirring was continued at room temperature overnight. Unreacted Boc-Phe, CDI and DIEA were removed by addition of 90 ml acetone to precipitate the $VB_{12}$. The product was then purified by Flash chromatography on a silica column (2.5× 50 cm) using a solvent mixture of 45% butanol, 30% propan-2-ol, 23% DW and 2% $NH_4$OH. The purified product was lyophilized and the dry powder deprotected by the addition of neat TFA (1 ml/100 mg) for 10 minutes. The product was then precipitated by the addition of ethyl acetate, and dried.

EXAMPLE 14
Preparation of ester-linked $VB_{12}$-glycine

Boc-glycine (1.57 g, 0.0059 mol) and carbonyl diimidazole (1.01 g, 0.0062 mol) were dissolved in DMF (6 ml) and the solution stirred at room temperature for 1 h with vigorous evolution of $CO_2$. A solution of $VB_{12}$ (1.0 g) in DMSO (10 ml) was added dropwise to the active ester solution followed by DIEA (1.2 ml, 0.89 g, 0.0069 mol) and stirring was continued at room temperature overnight. Unreacted Boc-Gly, CDI and DIEA were removed by addition of 90 ml acetone to precipitate the $VB_{12}$. The product was then purified by Flash chromatography on a silica column (2.5× 50 cm) using a solvent mixture of 45% butanol, 30% propan-2-ol, 23% DW and 2% $NH_4$OH. The purified product was lyophilized and the dry powder deprotected by the addition of neat TFA (1 ml/100 mg) for 10 minutes. The product was then precipitated by the addition of ethyl acetate, and dried.

EXAMPLE 15
Preparation of $VB_{12}$-glycine acid

Cyanocobalamin (1.0 g, 0.74 mmol) and 1,1'-carbonyldiimidazole (CDI, 260 mg) were added sequentially to dimethylsulfoxide (12 mL) at 30° C. and the mixture stirred for 25 min. OMe-Gly (2.7 mmol) was added in one portion followed by triethylamine (200 µL) and the mixture stirred for 24 h at room temperature. The mixture was poured into ethyl acetate (30 mL) and left to stand. The supernatant was poured off and the residue sonicated for 5 min in acetone (50 mL). The mixture was filtered and the solid washed with acetone. The residue was then dissolved in 0.1 M HCl solution and stirred for 30 min. The crude acid was then purified on Dowex 1×4 resin eluting with 2% acetic acid: yield, 95%; mp 239–242° C. (dec); TLC ($^i$PrOH 30/n-BuOH 45/$H_2$O 25/$NH_4$OH 2) $R_f$=0.41; MS (ESI) mass calcd for $C_{66}H_{90}N_{15}O_{17}CoP$ 1456, found 1456 (M)$^+$; UV ($H_2O$)$\lambda_{361}$ ($\epsilon$=19800).

EXAMPLE 16
Determination of the relative IF affinity of various 5'O-$VB_{12}$ derivatives.

Reagents

IF Buffer: BSA ($VB_{12}$ and IF deficient) BSA (Sigma A-3902) was dissolved at 1 mg/ml in 0.1M potassium phosphate buffer pH 7.5.

$^{57}$Co$VB_{12}$: $^{57}$Co stock (50 µl) (Kodak) was diluted into 50 ul of stock in 25 ml of IF buffer to give a solution of 1 ng $^{57}$Co$VB_{12}$/25 ml. 250 ng cold $VB_{12}$ was added to 25 ml of hot $^{57}$Co$VB_{12}$ solution to give a 10 ng/ml solution.

Porcine Intrinsic Factor: Porcine IF (Sigma) was dissolved in IF buffer at 200 Units/ml, and frozen in 500 ul lots (100 IU aliquots) until required.

BSA-coated charcoal: BSA (1%) was added to an equal volume of 5% charcoal solution of 0.1 M potassium phosphate buffer pH 7.5 and stirred gently for 30 minutes.

Procedure:

Ten fold up dilutions of $VB_{12}$ or $VB_{12}$ derivatives were prepared down to 1 ng/ml in IF buffer. An equal volume of diluted IF was added to each sample and incubated for 20 minutes at room temperature. An equal volume of the BSA-coated charcoal was added to each sample, which was mixed prior to centrifugation. Following centrifugation the supernatant and pellet of each sample were separated and $^{57}$Co$VB_{12}$ determined by counting in a gamma counter. Data is represented as the % inhibition of $^{57}$Co$VB_2$ binding when compared to unmodified $VB_{12}$.

| Compound | % binding relative to vitamin $B_{12}$ |
| --- | --- |
| hexyl-5'O-$VB_{12}$ | 49 |
| dodecyl-5'O-$VB_{12}$ | 35 |
| tetradecyl-5'O-$VB_{12}$ | 4.2 |
| hexadecy-5'O-$VB_{12}$ | 0.78 |
| octadecyl-5'O-$VB_{12}$ | 0.57 |
| aminoethyl-5'O-$VB_{12}$ | 40 |
| aminobutyl-5'O-$VB_{12}$ | 27 |
| t-butyl-Phe-5'O-$VB_{12}$ | |
| aminohexyl-5'O-$VB_{12}$ | 25 |
| aminododecanyl-5'O-$VB_{12}$ | 31 |
| succinylhydrazidyl-5'O-$VB_{12}$ | 37 |
| adiphylhydrazidyl-5'O-$VB_{12}$ | 29 |
| phenylalanyl-5'O-$VB_{12}$ | |
| glycyl-5'O-$VB_{12}$ | |
| HO-Gly-5'O-$VB_{12}$ | 25 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Russell-Jones G. J. The use of the vitamin $B_{12}$ transport system as a carrier for the oral delivery of peptides, proteins and nanoparticles. *Proc. 23 rd International Symposium on Controlled Release of Bioactive Materials*, 1996.
2. Anton, D. L. Hogenkamp, H. P. C., Walker, T. E., and Matwiyoff, N. A. Carbon-13 nuclear magnetic resonance studies of monocarboxylic acids of cyanocobalamin. Assignments of the b-, d-, and e-monocarboxylic acids. *J. Am. Chem. Soc.*, 102: 2215, 1980.
3. Russell-Jones, G. J., Westwood, S. W. and Habberfield, A. D. Vitamin $B_{12}$ mediated oral delivery systems for Granulocyte-Colony Stimulating Factor and erythropoietin. *Bioconj Chem*, 6, 459–465, 1995.
4. Toraya, T. and Fukui, S. The synthesis of several immobilized derivatives of vitamin $B_{12}$ coenzyme and their use as affinity absorbents for a study of interactions of diol dehydrase with the coenzyme. *J. Biol. Chem.*, 255, 3520, 1980.
5. Annunziato, M. E., Patel, U. S., Ranade, M., and Palumbo, P. S. p-Maleimidophenyl isocyanate: A novel heterobifunctional linker for hydroxyl to thiol coupling. *Bioconj. Chem.*, 4, 212, 1993.
6. Westwood, S. W., and Russell-Jones, G. J. Vitamin $B_{12}$ mediated delivery systems for GCSF and EPO. U.S. patent application Ser. No. 08/064,873; U.S. Pat. No. 5,548,064), 1993.
7. Habberfield, A. D., Kinstler, O. B., and Pitt, C. G. Conjugates of $VB_{12}$ and proteins. U.S. Pat. No. 5,574, 018) 1996.

We claim:

1. A method for preparing $VB_{12}$ derivatives suitable for linking to a polymer, nanoparticle or therapeutic agent, protein or peptide, comprising the steps of reacting the 5'OH group of $VB_{12}$ or an analogue thereof with a bifunctional carbonyl electrophile to form an active intermediate, and subsequently reacting the intermediate with a nucleophilic spacer molecule to yield said $VB_{12}$ derivative.

2. A method of claim 1, wherein the bifunctional carbonyl electrophile is selected from the group consisting of carbonyldiimidazole, phosgene, triphosgene, N,N'-disuccinimidyl carbonate, carbonyl dipiperidine, 1,1'-carbonyldi(1,2,4-triazole), di(2-pyridyl)ketone and di(1-benzotriazolyl)carbonate.

3. A method of claim 2, wherein the bifunctional carbonyl electrophile is carbonyldiimidazole.

4. A method of claim 1, wherein the nucleophilic spacer molecule is an amino or hydrazidyl spacer molecule substituted with any group selected from $C_{1-24}$alkyl, $C_{2-24}$alkenyl, $C_{2-24}$alkynyl, $C_{3-8}$cycloalkyl, ($C_{3-8}$cycloalkyl)alkyl, amino, —($C_{1-12}$alkyl)C(O)$R^2$, —($C_{2-12}$alkenyl)C(O)$R^2$, —$C_{1-8}$alkyl-C(O)NHNH$_2$ or —CH($R^3$)C(O)$R^4$, all of which are optionally substituted by one or more groups selected from amino, amido, hydroxy, alkyl, halo, haloalkyl, carboxy, alkoxycarbonyl, acetoxy, sulfanyl, aryl, arylalkyl and alkylarylalkyl, wherein, $R^2$ is amino, hydroxy, $C_{1-6}$alkoxy or $C_{2-6}$alkenyloxy, $R^3$ is an amino acid side chain or a derivative thereof, and $R^4$ is hydroxy, $C_{1-6}$alkoxy, an amino acid or a peptide.

5. A method of claim 4, wherein the spacer molecule is octadecylamine.

6. A method of claim 4, wherein the spacer molecule is diaminoethane.

7. A method of claim 4, wherein the spacer molecule is diaminobutane.

8. A method of claim 4, wherein the spacer molecule is diaminohexane.

9. A method of claim 4, wherein the spacer molecule is diaminododecane.

10. A method of claim 4, wherein the spacer molecule is diaminooctadeccane.

11. A method of claim 4, wherein the spacer molecule is an amino acid or a peptide.

12. A method of claim 4, wherein the spacer molecule is a dihydrazide.

13. A method of claim 12, wherein the dihydrazide is succinic acid dihydrazide.

14. A method of claim 12, wherein the dihydrazide is adipic acid dihydrazide.

15. A method for preparing a $VB_{12}$ derivative suitable for linking to a polymer, nanoparticle or therapeutic agent, protein or peptide comprising the steps of reacting a carboxylic acid spacer molecule with a bifunctional carbonyl electrophile to form an active intermediate, and subsequently reacting the 5'OH group of $VB_{12}$ with the active intermediate to yield said $VB_{12}$ derivative.

16. A method of claim 15, wherein the bifunctional carbonyl electrophile is selected from the group consisting of carbonyldiimidazole, phosgene, triphosgene, N,N'-disuccinimidyl carbonate, carbonyl dipiperidine, 1,1'-carbonyldi(1,2,4-triazole), di(2-pyridyl)ketone and di(1-benzotriazolyl)carbonate.

17. A method of claim 16, wherein the bifunctional carbonyl electrophile is carbonyldiimidazole.

18. A method of claim 15, wherein the carboxylic acid spacer molecule is N-Boc-Phe.

19. A method of claim 15, wherein the carboxylic acid spacer molecule is N-Boc-Gly.

20. A $VB_{12}$ derivative prepared by a method of claim 1 or claim 15.

21. A $VB_{12}$ derivative of the formula (I):

$$VB_{12}\text{-5'O—CO—NH—}R^1 \qquad (I)$$

or a salt thereof, wherein $R^1$ is $C_{1-24}$alkyl, $C_{2-24}$alkenyl, $C_{2-24}$alkynyl, $C_{3-8}$cycloalkyl, ($C_{3-8}$cycloalkyl)alkyl, amino, —($C_{1-}$ alkyl)C(O)R², —(C₂₋₁₂alkenyl)C(O)R², —NHC(O)—C₁₋₈alkyl-C(O)NHNH₂ or —CH(R³)C(O)R⁴ all of which are optionally substituted by one or more groups selected from amino, amido, hydroxy, alkyl, halo, haloalkyl, carboxy, alkoxycarbonyl, acetoxy, sulfanyl, aryl, arylalkyl and alkylarylalkyl, R² is amino, hydroxy, C₁₋₆alkoxy or C₂₋₆alkenyloxy, R³ is an amino acid side chain or a derivative thereof, and R⁴ is hydroxy, C₁₋₆alkoxy, an amino acid or a peptide.

22. A VB₁₂ derivative of claim 21, wherein R¹ is hexyl, dodecyl, tetradecyl, hexadecyl, octadecyl, aminoethyl, aminobutyl, aminohexyl, aminododecanyl, t-butyl-Phe, succinylhydrazidyl, adipylhydrazidyl, Gly-OMe or Gly-OH.

23. A VB₁₂ derivative of the formula (II):

VB₁₂-5'O—CO—R¹    (II)

or a salt thereof, wherein

R¹ is C₁₋₂₄alkyl or C₂₋₂₄alkenyl which are optionally substituted by one or more groups selected from amino, amido, hydroxy, alkyl, halo, haloalkyl, carboxy, alkoxycarbonyl, acetoxy, sulfanyl, aryl, arylalkyl and alkylarylalkyl, or R¹ is —CH(R²)—NHR³, R² is an amino acid side chain or derivative thereof, and R³ is hydrogen, an amine protecting group, an amino acid or a peptide.

24. A VB₁₂ derivative of claim 23, wherein R¹ is C₈₋₂₄alkyl or C₈₋₂₄alkenyl.

25. A VB₁₂ derivative of claim 23, wherein R¹ is —CH(R²)—NHR³, R² is Gly and R³ is Boc or hydrogen.

26. A VB₁₂ derivative of claim 23, wherein R¹ is —CH(R²)—NHR³, R² is Phe and R³ is Boc or hydrogen.

* * * * *